(12) United States Patent
Peterman

(10) Patent No.: US 12,013,343 B2
(45) Date of Patent: *Jun. 18, 2024

(54) ALDEHYDE DETECTION AND ANALYSIS USING SURFACE-ENHANCED RAMAN SPECTROSCOPY

(71) Applicant: OndaVia, Inc., Hayward, CA (US)

(72) Inventor: Mark Charles Peterman, Fremont, CA (US)

(73) Assignee: OndaVia, Inc., Hayward, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 17/226,884

(22) Filed: Apr. 9, 2021

(65) Prior Publication Data

US 2021/0239619 A1    Aug. 5, 2021

Related U.S. Application Data

(63) Continuation of application No. 16/298,362, filed on Mar. 11, 2019, now Pat. No. 11,002,682.

(Continued)

(51) Int. Cl.
*G01N 21/65* (2006.01)
*G01N 1/38* (2006.01)
(Continued)

(52) U.S. Cl.
CPC ............. *G01N 21/658* (2013.01); *G01N 1/38* (2013.01); *G01N 1/44* (2013.01); *G01N 21/78* (2013.01); *G01N 33/1826* (2013.01)

(58) Field of Classification Search
CPC .......... G01N 1/38; G01N 1/44; G01N 21/658; G01N 21/78; G01N 33/1826
See application file for complete search history.

(56) References Cited

U.S. PATENT DOCUMENTS

| 5,266,498 A | 11/1993 | Tarcha et al. |
| 5,563,031 A * | 10/1996 | Yu ............................. C12Q 1/26 435/14 |

(Continued)

FOREIGN PATENT DOCUMENTS

| CN | 103439160 A | 12/2013 |
| WO | 2017198993 A1 | 11/2017 |

OTHER PUBLICATIONS

Raman spectroscopy chemistry libre text Angus et al, the Department of Education and University of California at Davis (Year: 2022).*

(Continued)

*Primary Examiner* — Christine T Mui
*Assistant Examiner* — Jonathan Bortoli

(57) ABSTRACT

A hand-held microfluidic testing device is provided that includes a housing having a cartridge receiving port and a cartridge for input to the cartridge receiving port. An optical detection system in the housing is capable of providing an illuminated electric field useful for Raman spectroscopy. The cartridge may have a sample well. The sample well is loaded with a mixture of water containing the analyte, Raman-scattering nanoparticles and a calibration solution. The calibration solution contains an analogue of the analyte differing in its Raman response, for example an isotope of the analyte. Optionally, a chemical compound capable of increasing interaction between the analyte and the nanoparticles may be added.

7 Claims, 13 Drawing Sheets

Related U.S. Application Data

(60) Provisional application No. 62/641,529, filed on Mar. 12, 2018.

(51) Int. Cl.
  *G01N 1/44* (2006.01)
  *G01N 21/78* (2006.01)
  *G01N 33/18* (2006.01)

(56) References Cited

U.S. PATENT DOCUMENTS

| | | | |
|---|---|---|---|
| 6,174,677 | B1 | 1/2001 | Vo-Dinh |
| 6,972,173 | B2 | 12/2005 | Su et al. |
| 8,070,956 | B2 | 12/2011 | Peterman et al. |
| 8,702,976 | B2 | 4/2014 | Peterman |
| 9,863,924 | B2 | 1/2018 | Peterman et al. |
| 10,254,229 | B2 | 4/2019 | Peterman et al. |
| 2004/0058058 | A1 | 3/2004 | Shchegolikhin et al. |
| 2004/0110208 | A1 | 6/2004 | Chan et al. |
| 2004/0126279 | A1 | 7/2004 | Renzi et al. |
| 2004/0142484 | A1 | 7/2004 | Berlin et al. |
| 2004/0174520 | A1 | 9/2004 | Premasiri et al. |
| 2004/0191921 | A1 | 9/2004 | Farquharson et al. |
| 2006/0054506 | A1 | 3/2006 | Natan et al. |
| 2006/0061762 | A1 | 3/2006 | Dwight et al. |
| 2006/0144786 | A1 | 7/2006 | Lin et al. |
| 2006/0164636 | A1 | 7/2006 | Islam et al. |
| 2006/0166302 | A1 | 7/2006 | Clarke et al. |
| 2006/0240401 | A1 | 10/2006 | Clarke et al. |
| 2006/0257968 | A1 | 11/2006 | Van Duyne et al. |
| 2006/0260941 | A1 | 11/2006 | Tan et al. |
| 2006/0262303 | A1 | 11/2006 | Bonne et al. |
| 2007/0010026 | A1 | 1/2007 | Nguyen et al. |
| 2007/0059203 | A1 | 3/2007 | Burrell et al. |
| 2007/0127019 | A1 | 6/2007 | Zribi et al. |
| 2007/0155020 | A1* | 7/2007 | Su .................. G01N 33/54373 702/19 |
| 2007/0224683 | A1 | 9/2007 | Clarke et al. |
| 2007/0236697 | A1 | 10/2007 | Zribi et al. |
| 2008/0316480 | A1 | 12/2008 | Zhong et al. |
| 2009/0053818 | A1 | 2/2009 | Zhang et al. |
| 2011/0207231 | A1 | 8/2011 | Natan et al. |
| 2011/0266429 | A1 | 11/2011 | Vestel et al. |
| 2013/0271758 | A1 | 10/2013 | Marchant et al. |
| 2013/0323856 | A1 | 12/2013 | Martel et al. |
| 2014/0186939 | A1 | 7/2014 | Peterman et al. |
| 2014/0260708 | A1 | 9/2014 | Harrell et al. |
| 2015/0218615 | A1* | 8/2015 | Siegel .................. G01N 33/58 435/21 |
| 2017/0074799 | A1* | 3/2017 | Peterman ............. G01N 33/182 |
| 2019/0257760 | A1 | 8/2019 | Peterman et al. |

OTHER PUBLICATIONS

Zong et al "Surface-Enhanced Raman Spectroscopy for Bioanalysis: Reliability and Challenges" Chem. Rev. 2018, 118, 4946-4980 (Year: 2018).*
EPSC Abstracts vol. 16, EPSC2022-1046, 202 Europlanet Science Congress 2022 (Year: 2022).*
English translation of JP2007218866A (Year: 2007).*
Beckers et al., "The Preparation of Background Electrolytes in Capillary Zone Electrophoresis: Golden Rules and Pitfalls," Electrophoresis, Jan. 2003, vol. 24 (3), pp. 518-535.
European Patent Application No. 16847409.6, Communication pursuant to Article 94(3) EPC dated Sep. 3, 2020.
European Patent Application No. 16847409.6, Extended European Search Report dated Mar. 6, 2019.
Henderson et al., "Appendix 1: Naturally Occuring Isotopes. Mass Spectrometry of Inorganic, Coordination and Organometallic Compounds: Tools—Techniques—Tips," John Wiley & Sons Ltd, 2005, pp. 235-246.
International Patent Application No. PCT/US2016/052178, International Preliminary Report on Patentability, dated Mar. 29, 2018.
International Patent Application No. PCT/US2016/052178, International Search Report and Written Opinion dated Nov. 18, 2016.
International Patent Application No. PCT/US2019/021778, International Preliminary Report on Patentability dated Sep. 15, 2020.
International Patent Application No. PCT/US2019/021778, International Search Report and Written Opinion dated Aug. 30, 2019.
Jencks et al., "Equilibrium Deuterium Isotope Effects on the Ionization of Thiol Acids," Journal of the American Chemical Society, Sep. 1971, vol. 93 (18), pp. 4433-4436.
Lee et al., "Amine-Functionalized Gold Nanoparticles as Non-Cytotoxic and Efficient Intracellular siRNA Delivery Carriers," International Journal of Pharmaceutics, Nov. 2008, vol. 364 (1), pp. 94-101.
Mark Peterman, "Rapid Contaminant Monitoring," OndaVia Inc., Oct. 2012, 27 pages.
Marz et al., "Towards A Quantitative SERS Approach-Online Monitoring of Analytes in a Microfluidic System with Isotope-Edited Internal Standards," Journal of Biophotonics, Mar. 2009, vol. 2 (4), pp. 232-242.
Ondavia, "Basic Analysis System," available at https://www.ondavia.com/basic, accessed Jul. 2017, 1 page.
Ondavia, "Monoethanolamine (MEA) Analysis Cartridge," available at https://www.ondavia.com/monoethanolamine, accessed Jul. 2017, 1 page.
U.S. Appl. No. 14/198,163, Final Office Action dated Apr. 30, 2018.
U.S. Appl. No. 14/198,163, Notice of Allowance dated Nov. 20, 2018.
U.S. Appl. No. 15/239,153, Notice of Allowance dated Nov. 30, 2018.
U.S. Appl. No. 15/792,165, Notice of Allowance dated Nov. 29, 2019.
U.S. Appl. No. 16/280,651, Final Office Action dated Mar. 3, 2021.
U.S. Appl. No. 16/298,362, Notice of Allowance dated Mar. 11, 2021.
U.S. Appl. No. 15/792,165, Non-Final Office Action dated Apr. 9, 2018.
U.S. Appl. No. 14/198,163, Final Office Action dated Jul. 18, 2017.
U.S. Appl. No. 14/198,163, Non-Final Office Action dated Nov. 24, 2017.
U.S. Appl. No. 14/198,163, Office Action dated Apr. 7, 2016.
U.S. Appl. No. 14/198,163, Office Action dated Jan. 8, 2016.
U.S. Appl. No. 14/198,163, Office Action dated Jan. 19, 2017.
U.S. Appl. No. 14/198,163, Office Action dated Jul. 20, 2016.
U.S. Appl. No. 14/198,163, Office Action dated May 7, 2015.
U.S. Appl. No. 15/239,153, Non-Final Office Action dated Apr. 5, 2018.
U.S. Appl. No. 15/267,708, Non-Final Office Action dated Sep. 22, 2017.
U.S. Appl. No. 15/267,708, Notice of Allowance dated Nov. 15, 2017.
U.S. Appl. No. 15/792,165, Final Office Action dated Nov. 30, 2018.
U.S. Appl. No. 15/792,165, Non-Final Office Action dated Jun. 13, 2019.
U.S. Appl. No. 15/821,098, Non-Final Office Action dated Dec. 13, 2018.
U.S. Appl. No. 15/821,098, Notice of Allowance dated Jun. 6, 2019.
U.S. Appl. No. 16/280,651, Non-Final Office dated Aug. 12, 2020.
U.S. Appl. No. 16/870,530, Notice of Allowance dated Nov. 5, 2020.
U.S. Appl. No. 16/870,530, Notice of Allowance dated Sep. 21, 2020.
U.S. Appl. No. 16/560,579, Notice of Allowance dated Feb. 10, 2020.
Yazgan et al., "Detection of Melamine in Milk by Surfaceenhanced Raman Spectroscopy Coupled with Magnetic and Raman-Labeled Nanoparticles", Analytical and Bioanal Ytical Chemistry, Springer, Berlin, De, May 4, 2012, vol. 403(7). pp. 2009-2017.
Yin et al., "Quantitative Analysis of Mononucleotides by Isotopic Labeling Surface-Enhanced Raman Scattering Spectroscopy," Biosensors and Bioelectronics, 2011, vol. 26 (12), pp. 4828-4831.

(56) References Cited

OTHER PUBLICATIONS

Zhang et al., "Isotope Edited Internal Standard Method for Quantitative Surface-Enhanced Raman Spectroscopy," Analytical Chemistry, Apr. 2005, vol. 77 (11), pp. 3563-3569.
Bu and Lee., "Optical Properties of Dopamine Molecules with Silver Nanoparticles as Surface-Enhanced Raman Scattering (SERS) Substrates at Different pH Conditions," Journal of Nanoscience and Nanotechnology, Sep. 2013, vol. 13(9), pp. 5992-5996.
European Patent Application No. 16847409.6, Communication pursuant to Article 94(3) EPC dated Jul. 15, 2021.
European Patent Application No. EP19768679.3, Extended European Search Report dated Oct. 14, 2021.
Japanese Patent Application No. JP20210500012, Office action dated Dec. 9, 2022—English Translation available.
U.S. Appl. No. 17/118,482 , Notice of Allowance dated Apr. 28, 2022.
U.S. Appl. No. 16/280,651 Non-Final office action dated Aug. 17, 2021.
U.S. Appl. No. 17/118,482, Non-Final Office Action dated Jan. 28, 2022.
U.S. Appl. No. 16/975,305, Non Final office Action dated Apr. 26, 2022.
U.S. Appl. No. 17/527,844, Non Final Office Action dated Dec. 13, 2022.
U.S. Appl. No. 17/527,828, Non Final Office Action dated Dec. 13, 2022.
U.S. Appl. No. 16/975,305, Non-Final office Action dated Dec. 30, 2022.
U.S. Appl. No. 16/975,305, Final Office Action dated Apr. 20, 2023.
Canadian Patent Application No. 3,036,790, Office Action dated Mar. 21, 2023.
Japanese Patent Application No. 2021-500012, Written Opinion dated May 25, 2023.
European Patent Application No. 19768679.3, Office Action dated Jun. 23, 2023.
European Patent Application No. 16847409.6, Office Action dated Jun. 6, 2023.
Japanese Patent Application No. JP2021-500012, Office Action dated Aug. 22, 2023.

\* cited by examiner

ALDEHYDE DETECTION AND ANALYSIS USING SURFACE-ENHANCED RAMAN SPECTROSCOPY

RELATED APPLICATIONS

This application is a continuation of U.S. application Ser. No. 16/298,362, filed Mar. 11, 2019 which claims the benefit of U.S. Application Ser. No. 62/641,529, filed Mar. 12, 2018. U.S. Application Serial Nos. 16/298,362 and 62/641,529 are incorporated by reference.

FIELD OF THE INVENTION

The present invention relates to the detection, speciation and/or quantification of analytes, for example aldehydes, in a fluid, for example environmental water, using surface-enhanced Raman spectroscopy.

BACKGROUND

Currently, the detection and measurement of many analytes at trace levels within a water sample requires complex laboratory equipment and a skilled technician. A variety of laboratory techniques exist. The EPA provides a list of available and approved techniques for compounds of concern. The American Public Health Association, American Water Works Association, and Water Environmental Federation publish Standard Methods for the Examination of Water and Wastewater—an extensive treatise on water analysis methodology. Although a variety of analytical detection methods can be used in water analysis, most trace-level analysis falls upon widely-used and popular, yet complex and expensive, mass spectrometry methods.

Raman spectroscopy is a potential alternative for trace analyte detection. Raman spectroscopy provides a chemical signature for a compound (in the form of a unique configuration of peaks in the reflected spectrum), but the Raman signal is typically too weak for part-per-billion detection. However, the Raman signal can be enhanced by the presence of an active surface or marker (typically a metal), creating surface-enhanced Raman spectroscopy (SERS). With an adequate interaction between the analyte and the surface, signal enhancement creates opportunities to detect very small concentrations. Some compounds, such as pyridine, naturally interact strongly with gold and silver surfaces. In some other cases a binding compound may bring the analyte and metal molecules into sufficiently close contact. For example, treatments with octadecylthiol have been used successfully for SERS on planar substrates with some analytes.

In some SERS techniques, the surface is provided by metal nanoparticles. When a metallic nanoparticle smaller than the wavelength of light is introduced into the sample, the illuminating electric field will create surface resonances if there are free electrons in the nanoparticle. The nanoparticles can be gold, silver, or copper beads, for example. These oscillating charges create an enhanced local electric field along certain directions, which results in a much stronger Raman response. "Hot spot" regions can be created where the SERS signal is greatly enhanced. These regions are most likely due to nanoparticle alignments or aggregates that create even larger electric field enhancements.

U.S. Pat. No. 8,070,956, Hand-Held Microfluidic Testing Device, describes a testing device with a cartridge receiving port for receiving a cartridge. An optical detection system in the housing is disposed to analyze a sample in channel of the cartridge. In some embodiments, markers such as gold nanoparticles are present in the channel and the optical detection system is a Raman spectroscopy system. In some embodiments, the channel includes narrow sections along a microfluidic separation channel that trap gold nanoparticles at a high density. This encourages the creation of "hot spots" through nanoparticle density at a predetermined detection location.

Although some researchers have achieved remarkable detection limits using SERS, the use of SERS to measure the concentration of a trace analyte is less developed. In general, Raman signal strength is proportional to the amount of analyte per unit area. However, one issue is that the generation of random nanoparticle hot spots leads to random signal enhancements, which interferes with correlating signal strength to analyte concentration. Another issue is that aqueous sample conditions other than analyte concentration, for example pH, can alter the analyte signal strength.

INTRODUCTION

This specification describes the use of surface-enhanced Raman spectroscopy (SERS) to measure the concentration of various analytes, for example in an industrial or environmental water sample. In at least some cases, the composition of trace compounds is measured to within 10% accuracy. A measurement method uses an internal standard in the form of a known quantity of a reference compound added to a known volume of an aqueous mixture containing the analyte. The reference compound reacts similarly to the analyte under investigation with the surface but produces a different Raman spectrum. The reference compound may be, for example, an isotopologue, isomer, or enantiomer of the analyte or of a compound similar to the analyte. The reference compound is added to the mixture in an amount similar to the expected amount of the analyte.

A portable testing device is described having reusable and consumable components. The reusable components include a Raman spectroscopy instrument having a cartridge holder and software for operating the Raman spectroscopy instrument, optionally stored in a general-purpose computer. The consumable components include a cartridge, a dispersion of Raman-scattering nanoparticles and one or more reagents for the analyte under investigation. The one or more reagents, typically provided in solution, include a reference compound for the analyte and, optionally, one or more chemical compounds capable of increasing interaction between the analyte and the Raman-scattering nanoparticles. The cartridge has a cavity adapted to hold a mixture of the analyte, nanoparticles and one or more reagents in a suitable location in the Raman spectroscopy instrument. In some embodiments, the device may also include a solid-phase extraction column or other pretreatment devices or chemicals.

In use, a mixture is prepared of a water sample containing the analyte under investigation, the nanoparticles and the one or more reagents. At least some of the mixture is placed on the cartridge. The cartridge is loaded into the Raman spectroscopy instrument. The computer controls the Raman spectroscopy instrument to produce a Raman spectrum of the mixture. The produced spectrum includes individual spectra for the analyte and the reference compound. A ratiometric analysis of the individual spectra, typically performed by the software, is used to calculate the concentration of the analyte.

In some cases, the reference standard is an isotopologue of the analyte, or an isotopologue of a compound chemically similar to the analyte. When using the word "isotopologue" we mean to refer (unless clear from the context otherwise) to a form of a compound that differs in number of neutrons from the most common naturally occurring form of that compound. The word "isotope" may also be used for brevity or convenience with the same meaning even though, strictly speaking, the word isotope should be used with elements rather than molecules. Isotopologues of a compound have Raman spectra that are different from the commonly occurring form of the compound. The substitution of deuterium for hydrogen in a pyridine molecule, for example, results in a SERS spectrum with essentially the same intensity but with shifted peaks.

In the case of an analyte that is a molecular ion, a chemically similar compound may be another molecular ion having the same type and number of electron acceptors attached by the same type of bonds but to a different electron donor. In the case of an analyte with a functional group that is naturally SERS active under at least some conditions, such as an amine, a chemically similar compound may be a compound with the same functional group.

The Raman spectrum generated by the reference standard is produced and recorded simultaneously with the spectrum generated by the analyte in a composite spectrum. The Raman intensity of one or more bands corresponding to a known amount (i.e. concentration) of the reference standard is used as a reference against which the Raman intensity of one or more bands corresponding to the analyte is converted into a measurement of the amount (i.e. concentration) of the analyte. In some cases, optional adjustments may be made to accommodate factors such as the natural occurrence of the isotope or impurity of the added isotope. The reference standard preferably interacts with a SERS substrate (such as a gold nanoparticle) similarly to the analyte of interest. Thus both the reference standard and analyte show similar changes in signal strength due to "hot spots" or variations in sample composition. Therefore, when the Raman spectrum for the analyte (i.e. the intensity of one or more of its characteristic bands) is scaled with reference to the Raman spectrum for the reference standard (i.e. the intensity of one or more of its characteristic bands), an accurate quantification is achieved.

In some cases, an isotopologue used as a reference standard may be made by synthesizing a compound with, for example, a hydrogen isotope (i.e. deuterium) or an oxygen isotope (i.e. $^{18}O$). Replacing some or all of the hydrogen with deuterium causes a shift in the peaks of the Raman spectrum for many compounds, including amines like monoethanolamine, methylamine, diethanolamine, cyclohexylamine, morpholine and methyldiethanolamine, and hydrocarbons like benzene, toluene, ethylbenzene, and xylene. Replacing at least some, but preferably all, of the oxygen with heavy oxygen (typically $^{18}O$) causes a shift in the peaks of the Raman spectrum for many molecular ions, perchlorate, sulfate and selenate ions, for example.

Some analytes may be inherently SERS active—i.e., they interact naturally with a SERS substrate to produce a strong signal. In other cases, analytes may be made to interact with a SERS substrate by the addition of a binding reagent or adjustment of the general sample conditions such as pH or ionic strength. In yet other cases, a reaction involving the analyte is used to produce or consume a more SERS active compound. The more SERS active compound could be a more inherently active compound or a compound that can be more easily made to interact with a SERS substrate by way of a binding agent.

The amount of the more SERS active compound after the reaction can be measured and compared to a known amount of the more SERS active compound, if any, that was present before the reaction started. An internal standard for the more SERS active compound can be used to increase the accuracy of the measurement. The amount of the more SERS active compound that is consumed or created in the reaction can then be used to calculate the concentration of the analyte using a formula for the reaction.

DETAILED DESCRIPTION

Figure 1:
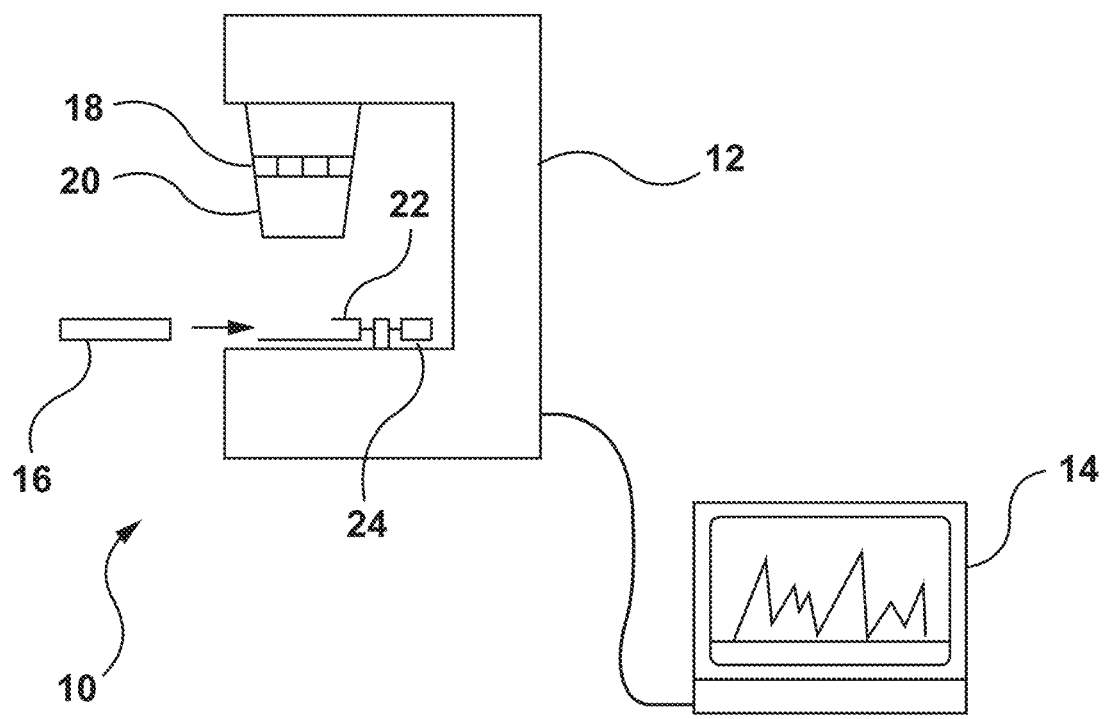
FIG. 1 is a schematic drawing of a portable SERS analysis system.
Figure 2:
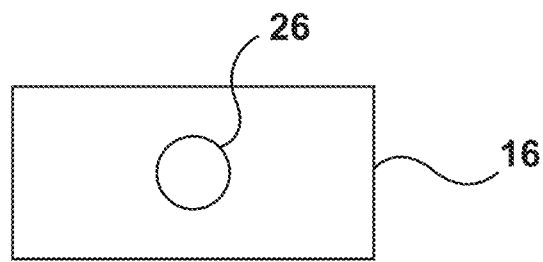
FIG. 2 is a top view of a cartridge for use with the system of FIG. 1.

An exemplary water analysis system described herein can be used to provide on-site or in-field analysis of aqueous samples. In general, a technician collects a water sample, processes that sample for analysis, and then introduces the sample to a cartridge. The cartridge is inserted into a Raman spectroscopy device, which may be operated through an interface provided by a general-purpose computer. Optics and electronics within the Raman spectroscopy device produce a Raman spectrum for the sample which is analyzed, for example with software in the general-purpose computer, to determine the concentration of an analyte under investigation in the water sample.

Raman spectroscopy allows analytes to be detected by their specific "fingerprint", or pattern of peaks in the Raman spectrum. Preferably, a known amount of a reference compound is present in the sample with the analyte when the Raman spectrum is produced and provides an internal calibration standard against which signal intensity of the analyte may be compared to provide accurate quantitative results. The intensity of a Raman signal scales with (i.e. is proportional to) the number of molecules present per unit area. When a known amount of calibration standard is introduced to a sample aqueous solution of known volume containing the analyte, the quantity of analyte may be determined by comparing the signal intensity of the calibration standard and the analyte, for example through ratiometric methods.

The specific ratiometric method used is not critical. For example, the concentration of the reference compound in the sample can be divided by the intensity of the highest peak in the spectrum for the reference compound to provide a correlation factor. Multiplying this correlation factor by the intensity of the highest peak in the spectrum for the analyte produces the concentration of the analyte. Alternatively, the signal intensity of the analyte (i.e. the intensity within one or more bands characteristic of the analyte) can be divided by the signal intensity within corresponding bands of the reference compound to provide a scaling factor. Multiplying this scaling factor by the known concentration of the reference compound in the sample produces the concentration of the analyte. Optionally adjustments may be made for various factors such as the purity of the calibration standard, or natural occurrence of the calibration standard in the analyte. Other ordinary adjustments, such as smoothing the spectrum curve or subtracting background signals before measuring intensity, may also be made.

The reference compound may be added to the cartridge during manufacturing or added to a sample containing the analyte before the analyte is added to the cartridge. Similarly, SERS active metallic nanoparticles (i.e. markers) may be added to the cartridge during manufacturing or added to a sample containing the analyte before the analyte is added to the cartridge. Optionally, mixing a solution of the reference compound with an aqueous sample containing the analyte as a first step, or at least before loading the sample to the cartridge, allows a mixture of analyte and reference compound to be made using volumes larger than would fit in the cartridge. This can help with making an accurate calculation of the concentration of the reference compound in the mixture, particularly when making measurements in the field where high precision liquid handling devices are not available. Once the reference compound and analyte sample are mixed together, later errors such as spilling some of the mixture do not typically affect the accuracy of the analyte concentration measurement.

The reference compound is added to the mixture in an amount similar to the expected amount of the analyte. For example, if the analyte is expected to have a concentration in the range of 0-100 ppm, the analyte sample may be mixed with a solution of equal volume containing 25-75 ppm of reference compound. Similarly, if the analyte is expected to have a concentration in the range of 0-100 ppb, the analyte sample may be mixed with a solution of equal volume containing 25-75 ppb of reference compound. The amount of reference compound in the mixture is preferably within 0.1 to 10 times the amount of analyte in the mixture.

Optionally, the reference compound may be an isotopologue of the analyte under investigation. An isotopologue provides a powerful internal calibration standard as it differs from the analyte only in the number of neutrons. The chemical response and reaction of the reference compound will be nearly identical to the analyte. However, under Raman spectroscopy, the isotopologue has a different spectrum. Therefore, one can record the analyte and isotopologue spectra simultaneously, using ratiometric analysis of the composite spectrum to quantify the unknown analyte.

In another option, the calibration standard may be an isotope of a compound that is chemically similar to the analyte under study. For example, selenium and sulfur are chemically quite similar. A measurement of selenate may rely upon the measurement of sulfate, of a selenate isotope, or of a sulfate isotope as a calibration standard. In cases where an unknown amount of sulfate may exist in the sample, for example when testing flue gas desulfurization blowdown water, the use of a selenate isotope or sulfate isotope is preferred. Sulfate isotopes are typically easier to produce. When either a selenate or sulfate isotope is used, the concentration of sulfate in the sample can be measured simultaneously with a measurement of the selenate concentration.

Optionally, one or more additional compounds may be mixed with the sample to enhance interaction between the nanoparticles and both of the analyte and the reference compound. In some cases, the additional compound modifies the SERS marker, i.e. the nanoparticles. Optionally, the modification can be chosen for analyte specificity using compounds designed to interact preferentially or only with the analyte under investigation and the reference compound. This approach reduces interferences while increasing signal strength.

Optionally, an additional compound can include one or more compounds selected from: thiols, amines, silanes, polymeric particles, metallic particles, crown esters, cysteamine, cystamine, diethylaminethanethiol, mercaptopropionic acid, 1-propanethiol, octanethiol, octyldecanethiol, polystyrene, iron, or silica. In other options, the additional compound can be a compound effective to modify the pH or ionic strength of a mixture including the analyte and the nanoparticles. Some analytes interact with a SERS substrate more at a certain pH or in the presence of ions. Optionally, one or more additional compounds can be provided premixed with the reference compound in a reagent solution.

FIG. 1 shows an analysis system 10. The analysis system 10 includes a Raman spectroscopy unit 12, a computer 14 and a cartridge 16. The computer 14 may be a separate computer as shown or alternatively could be incorporated into the Raman spectroscopy unit 12. The computer 14 is preferably a portable general-purpose computer, for example a laptop, tablet or smart-phone.

The Raman spectroscopy unit 12 includes an optical detection system in a housing. The optical detection system is capable of providing an illuminating electric field, where the illuminating electric field is capable of being used for Raman spectroscopy, for example with Raman-scattering nanoparticles and the calibration solution, to analyze a sample under test input on or the cartridge 16. The Raman spectroscopy unit 12 further includes a lens 20 with a focus ring 18. The focus ring 18 allows the lens 20 to be focused on a sample contained in the cartridge 16. The Raman spectroscopy unit 12 includes a cartridge holder 22 adapted to receive the cartridge 16. The cartridge holder 22 can be translated relative to lens 20 by turning a screw 24. A second screw (not shown) is preferably provided orthogonal to screw 24 to allow a portion of the cartridge 16 at which a sample to be tested is visible to be aligned with the lens 20.

The cartridge 16 receives an aqueous mixture including the analyte. The cartridge 16 has a cavity 26, which receives the sample. The cartridge 16 may be plastic. However, if the mixture is expected to be transparent such that the Raman laser would penetrate through to the bottom of the cavity 26, the bottom of the cavity may be lined with a reflective surface such as stainless steel. The cartridge 16 may alternatively be a glass or plastic bag or vial or other suitable container. When the cartridge 16 is mounted in the cartridge holder 22, the cavity 26 is aligned with the lens 20.

In another option, the cartridge 16 can include one or more of nanoparticles, a reference compound, one or more additional compounds, microfluidic channels configured to provide an area with an increased density of nanoparticles, or microfluidic separation channels, for example as described in U.S. Pat. No. 8,070,956.

Figure 3:
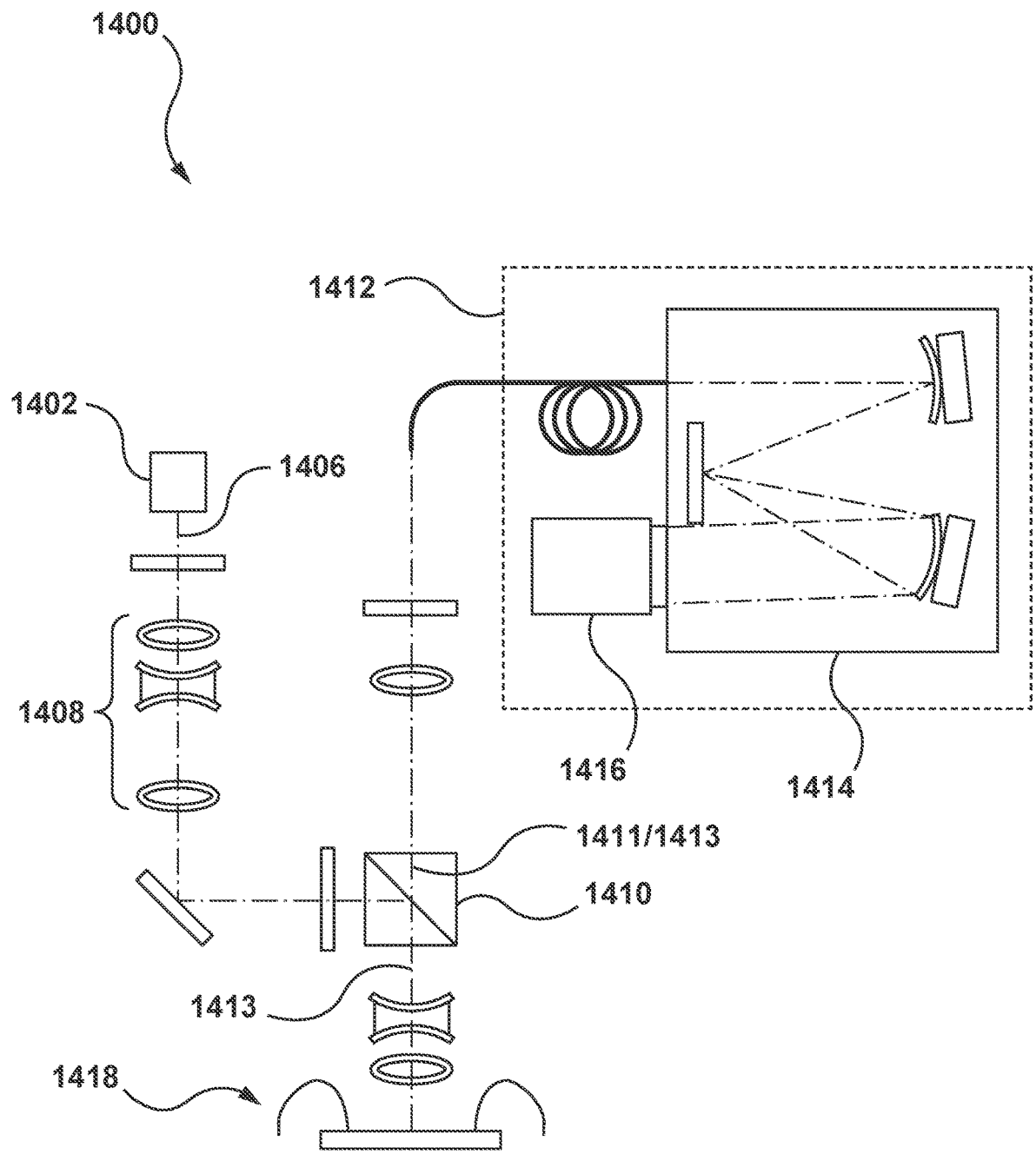
FIG. 3 shows an example optical system contained within the analysis instrument according to the present invention.

FIG. 3 shows an example optical system 1400, contained within the Raman spectroscopy unit 12. Shown is a light source 1402, such as a laser, projecting a light beam 1406 passing through a series of optics 1408 arranged as a beam expander that is reflected into a dichroic optic 1410 to direct the reference light beam 1411 into a spectrometer 1412 for analysis in a monochrometer 1414 and recordation in a CCD array 1416. The dichroic 1410 simultaneously directs the signal light beam 1413 to the cartridge 1418 to gather a signal from a sample in the cartridge 1418 and reflect the signal along the beam path into the spectrometer 1412 and CCD 1416 array for analysis.

Quantification of Amines

One important analyte category is the monitoring of amines, for example in industrial processes. Organic amines are used as corrosion control agents that increase pH and scavenge corrosive contaminants. Monoethanolamine (MEA), for example, is a widely used corrosion inhibitor that reduces dissolved $CO_2$ and helps control pH in industrial boilers and nuclear power plants. Amines are also effective as hydrogen sulfide scavengers in oil and gas production and processing. For example, MEA-triazine is frequently used as a hydrogen sulfide scavenger at the well-head. MEA or other compounds can also exist as tramp amines that affect refinery operations. On-site monitoring for amines, for example at a refinery, pipeline, or well-head, can help maintain appropriate corrosion protection while extending system lifetime and avoiding costly corrosion-induced shutdowns and failures.

The analysis system 10 described above may be operated to measure the concentration of an amine. Amines interact naturally with gold and silver substrates. Under basic pH conditions, the amine group will adhere to the nanoparticles, resulting in a strong Raman response. In some cases, the analysis method takes under five minutes, and may be performed in the field. In some cases, measurement of an amine in the ppb range is possible. However, in industrial process management, measurement of amines in the ppm range is more often required. In general, the concentration of an amine can be measured using an isotopologue of an amine as a reference compound, preferably an isotopologue of the same amine or an amine of similar molecular weight and structure. An analyte, isotopologue and nanoparticles mixture is preferably adjusted to a basic pH, for example a pH of at least 1 or preferably at least 2 higher than the pKa of the analyte amine, before measuring its Raman spectrum.

In one embodiment, a method provides part-per-million concentration measurement of methylamine in refinery process waters. Methylamine is a tramp amine that negatively impacts the refining process. The detection limit for methylamine in aqueous solutions is 20-ppb or better.

In another embodiment, the concentration of monoethanolamine (MEA) is determined. Rapid measurement of monoethanolamine is useful in controlling refinery operations. A preferred isotopologue for MEA is monoethanolamine-d4. pH of the MEA, isotopologue and nanoparticles mixture is preferably raised to 12.6 to 12.9. The mixture of MEA, isotopologue and nanoparticles is added to the cartridge and its Raman spectrum determined.

In a method described herein, a reference compound is added to an amine compound analyte sample. The reference compound is an isotopologue of the same or another amine compound. In one example, a known volume of methylamine-$d_3$ solution at 25- to 75-ppm is added to a sample of known volume (preferably the same or within 50% of the volume of methylamine-$d_3$ solution) having an unknown quantity of methylamine-$d_0$. The methylamine-$d_3$ creates a reference spectrum (within a composite spectrum) against which the methylamine-do spectrum may be quantified. This approach can result in ±10% measurement accuracy over a 0- to 100-ppm range of methylamine-do. Accuracy can be improved at the low end with a lower concentration methylamine-$d_3$ solution. pH of the mixture is preferably adjusted to 12.6 to 13.0 before taking its Raman spectrum.

Figure 4:
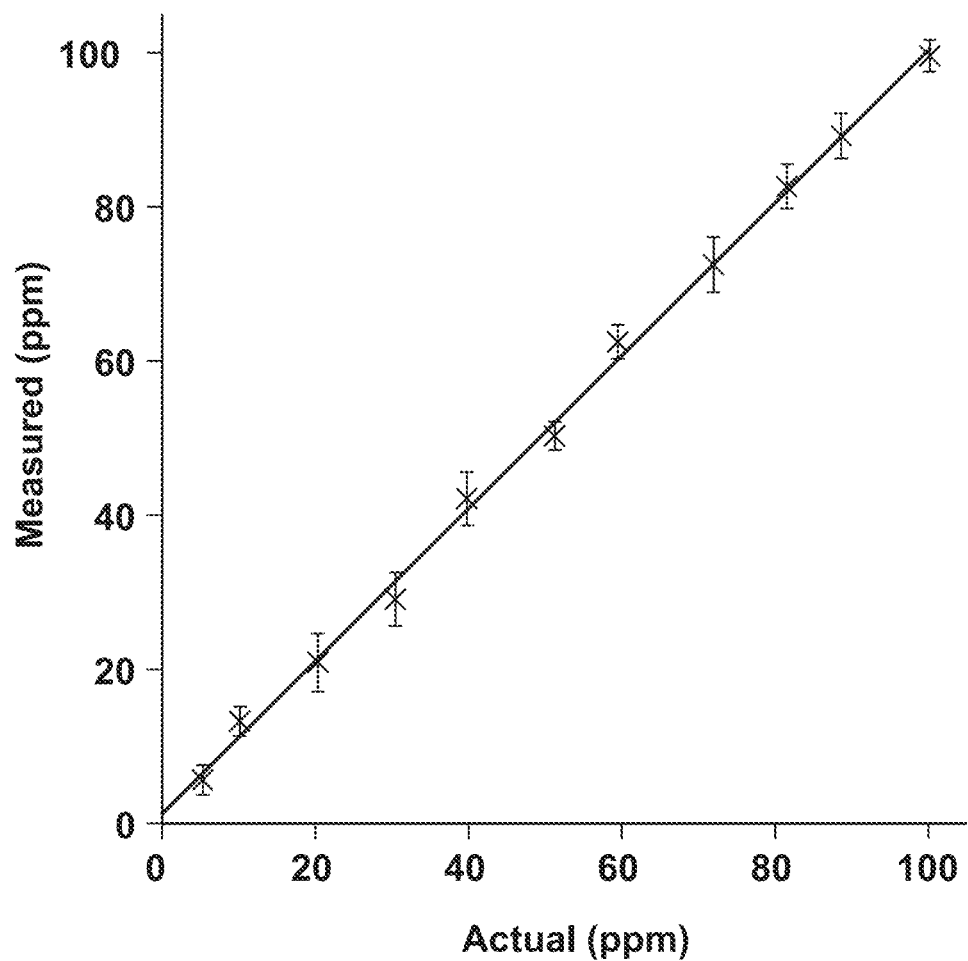
FIG. 4 is a calibration curve for diethanolamine showing the accuracy, linearity, and detection range.

In another example, diethanolamine-$d_8$ is used as an internal standard when measuring the concentration of diethanolamine. FIG. 4 shows a calibration curve prepared by measuring the concentration of samples of diethanolamine prepared at different concentrations with diethanolamine-$d_8$ used as an internal standard. The response is linear over 0- to 100-ppm, and the accuracy of the measured concentration is within 10%. pH of the mixture is preferably adjusted to 12.6 to 13.0.

In other examples, the approach described above is applied to triazine-based compounds. For example, accurate, ppm-level measurements of MEA-triazine or dithiazine can be achieved using an ethanolamine-$d_4$ or an MEA-triazine-$d_{12}$ isotopologue as a reference compound.

In further examples, the process for measuring one amine can be extended to measuring multiple amines. The internal standard can be a mixture of materials, for example ethanolamine-$d_4$ and methylamine-$d_3$. These two compounds individually are excellent internal standards for ethanolamine and methylamine individually. By including both isotopologues in a mixture, one can determine the concentration of ethanolamine and methylamine in a sample. First, the spectrum is scaled to the ethanolamine-$d_4$ peak at 870-$cm^{-1}$, and the ethanolamine concentration is determined. The same spectrum is then scaled to the 950-$cm^{-1}$ methylamine-$d_3$ peak, and the methylamine concentration is determined.

Furthermore, the spectrum for a first amine may be subtracted from the overall spectrum sequentially before analyzing the spectrum of a second amine to improve signal-to-noise ratio. For example, an ethanolamine spectrum is stronger than a methylamine signal. By subtracting the ethanolamine spectrum, one can improve the accuracy of methylamine analysis.

Use of an Intermediate Reaction

In yet other examples, a reaction involving the analyte is used to produce or consume a more SERS active compound. The amount of the more SERS active compound in the reaction product is measured to determine if SERS active compound was created or consumed. A reference compound for the more SERS active compound can be used to increase the accuracy of the measurement. The amount of the more SERS active compound that is consumed or created in the reaction can then be used to calculate the concentration of the analyte using a formula for the reaction.

In one example, the consumption of pyridine is used to determine the concentration of a gem-halogenated compound. The amount of gem-halogenated compound required to consume a certain amount of pyridine can be determined according the Fujiwara reaction, normally used in a colorimetric method for the detection of gem-halogenated compounds using pyridine. The gem-halogenated compound may be, for example, trichloroethylene, a trihalomethane, chloroform, or a haloacetic acid.

In one example, the concentration of a gem-halogenated compound, in particular trichloroethylene (TCE), is measured. A sample is taken of water suspected of containing TCE in the ppb range. The pH of the sample is adjusted to 12-13, for example by adding caustic, as needed for the Fujiwara reaction. Dilute pyridine solution, for example at about 100-150 ppb, is added in a 1:1 or similar volume ratio to the alkaline sample. The reaction of pyridine with TCE will progress, resulting in complete consumption of the TCE and a decrease in the pyridine concentration. We then add an internal standard, for example a solution of pyridine-$d_5$ of known concentration and volume, to the reaction product solution. When mixed with a SERS substrate such as gold nanoparticles, the resulting SERS signal will be a combination of pyridine-do and pyridine-$d_5$ signals. We then scale the signal to the main pyridine-$d_5$ peak, which is spectrally shifted from the main do peak, to determine the amount of pyridine-do remaining. Subtracting this value from the initial amount of pyridine gives the amount of pyridine consumed. This value can be used to calculate the amount of TCE that was present in the original sample. If there is no pyridine left after reaction then the test is inconclusive and must be repeated with a larger initial amount of pyridine.

Alternatively, a pyridine derivative such as nicotinamide may be used to determine the concentration of a gem-halogenated compound. Nicotinamide may offer benefits such as selectivity, usability, or safety. Pyrdine-$d_5$ may be used as an internal standard with a pyridine derivative, as may an isotopologue of the pyridine derivative.

In another example, the concentration of formaldehyde is measured by way of a reaction between an amine and formaldehyde. Cysteamine reacts with formaldehyde to create a thiazolidine. Cysteamine is also a thiol that interacts strongly with a gold substrate. A sample of formaldehyde is mixed with a known amount of cysteamine. The reaction completely consumes the formaldehyde and some of the cysteamine. This reacted product solution may then be mixed with a cysteamine isotopologue and gold nanoparticles. The ratio of cysteamine isotopologue to cysteamine provides a measure of cysteamine remaining, which can be used to determine the initial formaldehyde concentration. Alternatively, a thiazolidine isotopologue can be added to the reacted product solution to provide a measure of cysteamine remaining, which can be used to determine the initial formaldehyde concentration. In either case, the lack of any remaining cysteamine indicates a failure and that the method should be repeated starting with a larger amount of cysteamine. In these examples, cystamine may be used in place of cysteamine.

Quantification of Ions

The methods and equipment described above may also be adopted to measure the concentration of ions, for example molecular anions, in water. The concentration may be in the ppb range. In addition to a reference compound, a binding compound is used to increase interaction between the ion and the nanoparticles. The binding compound may be an amine, preferably with no more than 3 carbon atoms between a nitrogen atom and a sulfur atom, for example a thiol. A mixture of anylatc analyte, isotopologue, binding compound and nanoparticles is adjusted to an acidic pH, for example 5.0 or less. The preferred pH can be determined by trial and error, but varies with the pKa of the binding compound and can be estimated from the examples below adjusted to reflect the pKa of a different amine if used.

In one example, the concentration of perchlorate ions is measured. Perchlorate is a hydrophobic anion. By first modifying the surface of the SERS nanoparticles, i.e. gold nanoparticles, with a hydrophobic cationic species, we create a surface interaction between perchlorate and the nanoparticle. Under acidic conditions, amines become protonated, acting as a cationic treatment to draw anionic species to the nanoparticle. Thiol-based amine compounds like dimethylaminoethanethiol or diethylaminoethanethiol create such a surface. Other anions like sulfate or selenate that are not hydrophobic interact with SERS nanoparticles, i.e. gold nanoparticles, under the influence of less hydrophobic compounds such as cysteamine. The addition of an anionic isotopologue as an internal standard enables repeatable, accurate measurements.

Figure 5:
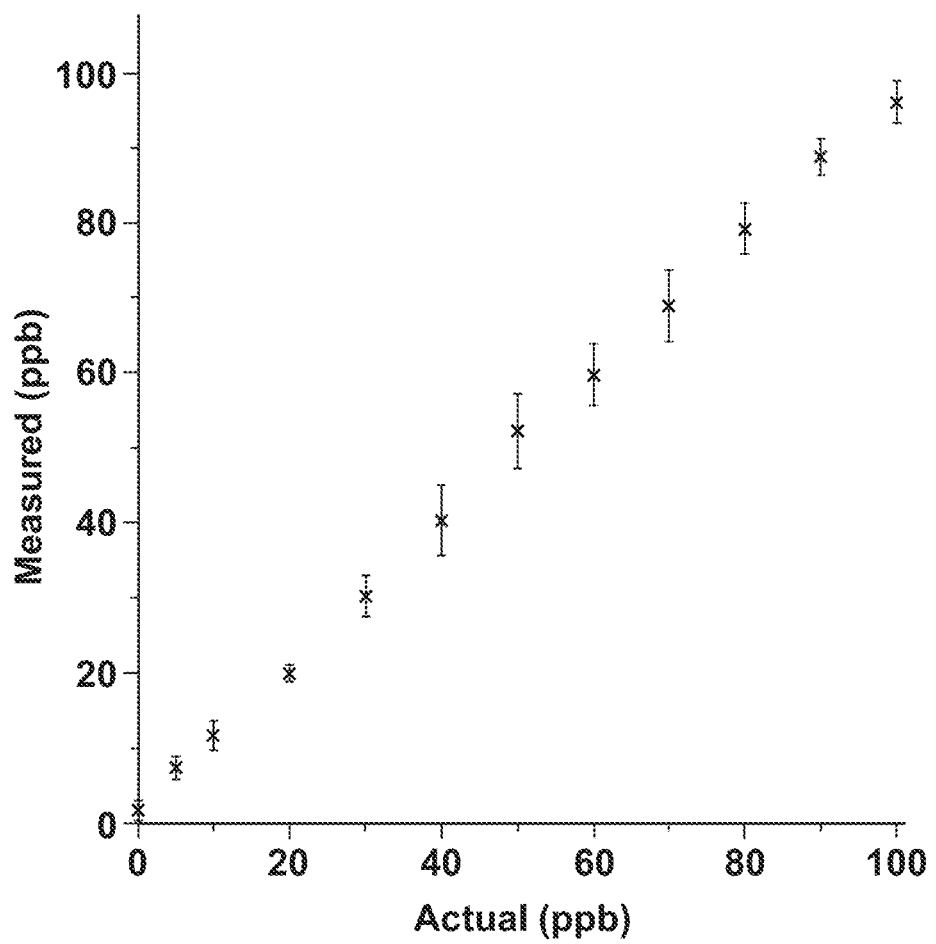
FIG. 5 is a calibration curve for perchlorate showing the accuracy, linearity, and detection range.

In a particular example of perchlorate measurement, the user starts with at 100-μl sample of water expected to contain perchlorate. To this sample, 10-μl of a 550-ppb perchlorate—$^{18}O_4$ solution is added, resulting in a final concentration of 50-ppb $Cl^{18}O_4$ in the sample. This sample is then adjusted to pH 1.8-3.0, preferably about 2.5 using hydrochloric acid. Next, a small quantity of methanol (10-μl) and a preferred thiol compound (dimethylaminoethanethiol) is added to the sample vial, followed by 5-μl of concentrated gold nanoparticles. This combined sample is allowed to dry on a clean, steel substrate, and then analyzed via Raman spectroscopy. The heavy perchlorate provides an internal standard against which the intensity of the perchlorate spectrum is compared. The resulting calibration curve is presented in FIG. 5. Measurement accuracies of 10% with 4-ppb detection limits are possible. A similar approach works for the detection and quantification of chromate, using the heavy-oxygen isotopologue of chromate as an internal standard.

Figure 6:
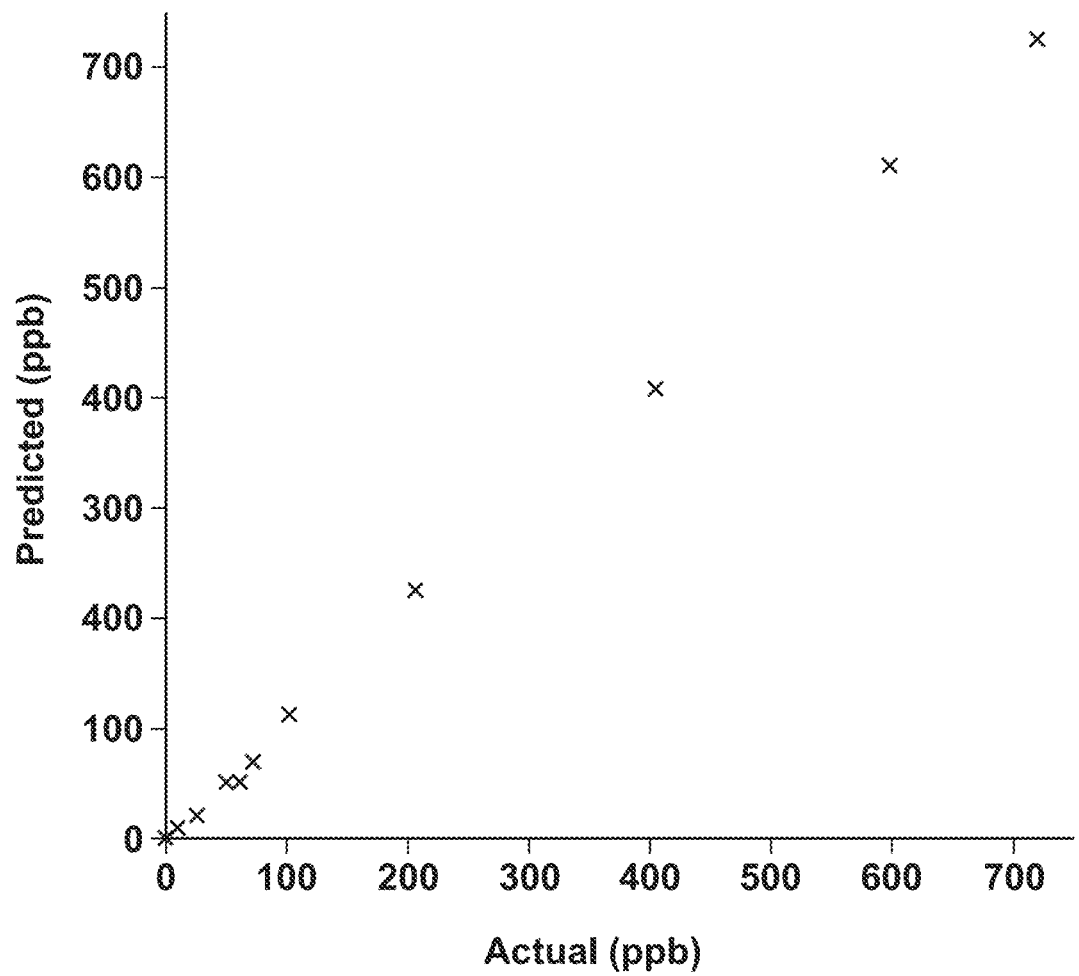
FIG. 6 is a calibration curve for selenate showing the accuracy, linearity, and detection range.

In cases where creation of the isotopologue would be unduly expensive or complicated, a similar anion can be used as a reference material. A similar anion preferably has the same number and kind of electron acceptors attached to an electron donor with the same type of bonds. For example, selenium and sulfur have very similar structures. The detection of selenate may be achieved by using sulfate or a selenate isotopologue (preferably with 4 $^{18}O$) as an internal standard, with cysteamine or cystamine as a nanoparticle surface treatment compound. The pH of the mixture of selenate, isotopologue, cysteamine or cystamine and SERS substrate (for example gold nanoparticles) is preferably adjust to about 3.5, for example by adding HCl. However, sulfate is a commonly occurring material, making a sulfate isotopologue (S $^{18}O_4$) a convenient internal standard. Furthermore, by using a sulfate isotopologue, both sulfate and selenate can by quantified simultaneously. A calibration curve of selenate measured using a sulfate isotopologue as an internal standard is presented in FIG. 6.

In preparing an isotopologue of a molecular anion, it is preferably to replace all of the O atoms with $^{18}O$. This requires a reaction driven to completion, which more easily creates a substantially pure isotopologue than a partial substitution of oxygen ions. The natural occurrence of such isotopologues is also rare and so adjustments are generally not required for isotopologue purity or naturally occurring isotopologues. However, the isotopologue should not be exposed to conditions that would cause it to revert to the naturally occurring form. For example, a selenate isotopologue with $^{18}O$ should not be stored in highly acidic water (i.e. pH of 1.0 or less) for an extended period of time since this will cause it to swap its heavy oxygen with oxygen in the water.

Although the nanoparticles may be pre-treated with an additional compound such as a thiol before adding the sample, it is preferable that the additional compound be mixed with the nanoparticles at about the same time the sample. This process increases response while improving product lifetime.

In other examples, addition of anionic compound, such as 3-mercaptopropionic acid, to nanoparticles enable the measurement of cationic ions in water. As discussed above, an internal reference standard for the cationic ions is preferably also added.

Quantification in Complex Matrices

In some cases, a measurement method as described above may be applied to analyte measurement in complex sample matrices. For example, refinery process waters may contain ppm-level amines in the presence of many salts and hydrocarbons. Pre-treatment methods can prepare the sample for analysis; however, pre-treatment can be challenging as it may affect the level of the analyte of interest. In these cases, adding the reference compound before treatment reduces errors caused by pre-treatment. The pre-treatment may be, for example, solid-liquid separation, ion exchange, strong anion exchange or ion extraction.

For example, the measurement of amines in refinery sour water presents a significant challenge. Sour water is defined by the presence of sulfide, which leads to the distinctive odor. These water samples, however, can also contain an array of other contaminants: ionic species, metals, organic acids, hydrocarbons, and amines, to name a few. Water collected from desalter operations, for example, may have high ion and amines levels (potentially more than 1000-ppm). Overhead water, in contrast, typically has contaminants levels below 100-ppm.

To analyze complex samples, the user first introduces the internal standard, such as an isotopologue, to the sample before sample pre-treatment. The sample pre-treatment will remove the analyte and the internal standard generally equally, enabling a precise concentration measurement after the pre-treatment. The pre-treatment is preferably a process to remove anions, for example an anion exchange or anion extraction process. The pH of the mixture of analyte and isotopologue is preferably reduced as required to keep the analyte and isotopologue in solution while undesirable anions are removed in the pretreatment process. Alternatively, the analyte and isotopologue maybe captured by passing the mixture through a cation extraction unit, discarding the remainder of the sample, and then eluting the analyte and isotopologue from the cation extraction unit.

Figure 7:
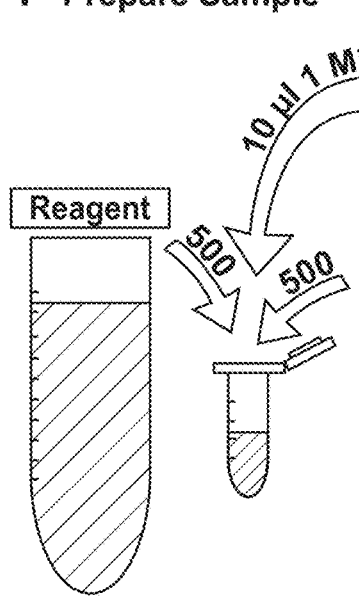
FIG. 7 shows a method for sample preparation in the analysis of amines in sour water.
Figure 7:
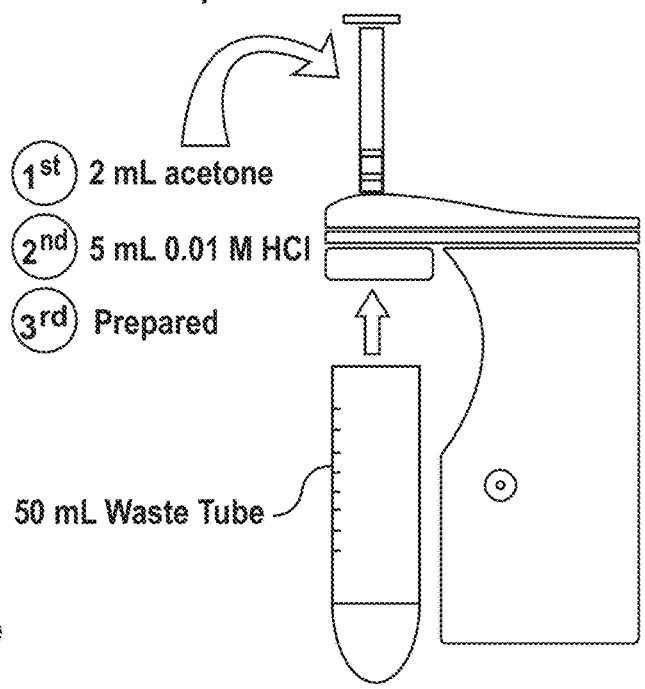
Figure 7:
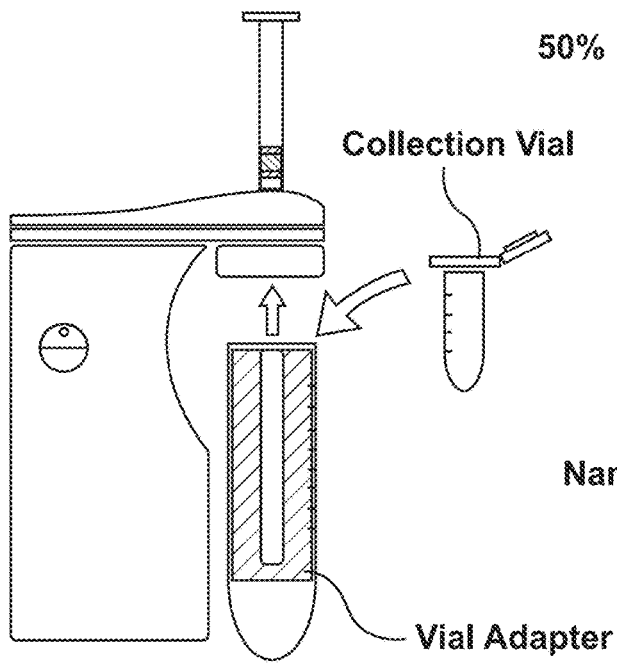
Figure 7:
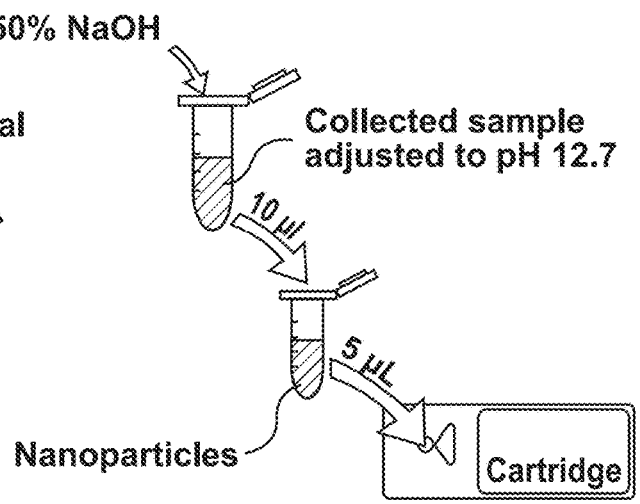

For sour water analysis, an exemplary sample preparation method is presented in FIG. 7. A solid-phase extraction (SPE) column designed for the removal of anions is first cleaned with 5-mL of 0.01 M HCl. The 500-µL sample is mixed 1:1 with a reagent solution containing the isotopologue. 10 µL of 1 M HCl is added to this mixture and then the mixture is introduced to the SPE column. The first 500-µL is discarded, and the remaining sample is collected. The pH of the remaining sample is adjusted upwards and then its Raman spectrum is measured.

Aldehydes

Metaldehyde is an active component in slug and snail bait. Drinking water limits in the UK and EU are 100 parts-per-trillion (ppt). The level in rivers depends on weather, season and geopgraphy. Analysis can be done via GC/MS.

Metaldehyde is a cyclic tetramer of acetaldehyde. It undergoes hydrolysis in a strong acid or when heated (i.e. to 70° C. or more) and converts to aldehyde.

Aldehyde concentration can be estimated by colorimetric analysis. MBTH (N-methylbenzothiazolinone-2-hydrazone) combines with C1-C3 aldehydes (i.e. formaldehyde, acetaldehyde, propionaldehyde (propanal), which are examples of compounds reactive with a colorimetric dye such as MBTH) to form a blue colored compound (which corresponds with a reaction product of the colorimetric dye and the compound reactive with the colorimetric dye) in solution. The MBTH is added to a water sample suspected of having aldehyde. After a wait time of 30 minutes, $Fe^{3+}$ is added to the sample. After 15 minutes, the color intensity is measured. However, colorimetric analysis cannot speciate and it does not allow for detection or concentration measurement at low levels.

MBTH contains multiple nitrogen and sulfur groups that can attach to gold. In the methods below, we add gold nanoparticles (i.e. 80-nm colloidal gold nanoparticles) to the sample. This allows analysis with a Raman spectrometer. An exemplary spectrometer has a 785-nm, 100-mW laser; 200-2000-$cm^{-1}$ with 4-$cm^{-1}$ resolution.

Figure 9:
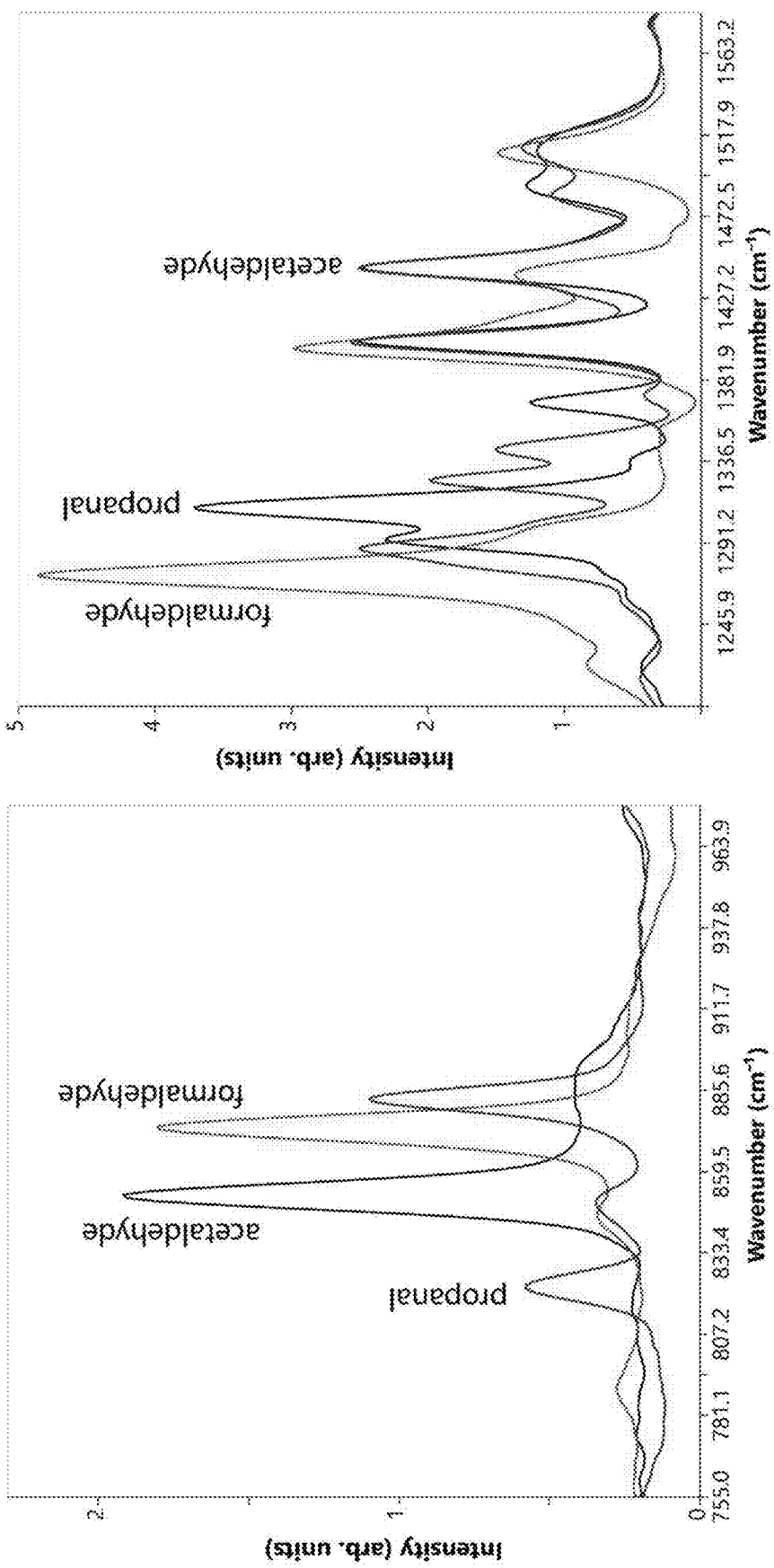
FIG. 9 shows portions of Raman spectra for aldehyde-MBTH compounds.

In a method of aldehyde analysis, a sample is prepared as in for colorimetric analysis, but analysed using Raman spectra rather than color analysis. In an example method: MBTH is added to a sample; wait, i.e. 30 minutes; add $Fe^{3+}$; wait, i.e. 15 minutes; mix with gold nanoparticles; measure the Ram spectrum. Although different aldehydes produce the same color when combined with MBTH, the Raman spectra of aldehyde-MBTH compounds are different. For example, compounds of MBTH with propanal, acetaldehyde and formaldehyde each produce a distinct peak in the range of 800 $cm^{-1}$ to 900 $cm^{-1}$, and another distinct peak in the range of around 1250-1500 $cm^{-1}$ (see FIG. 9).

Figure 10:
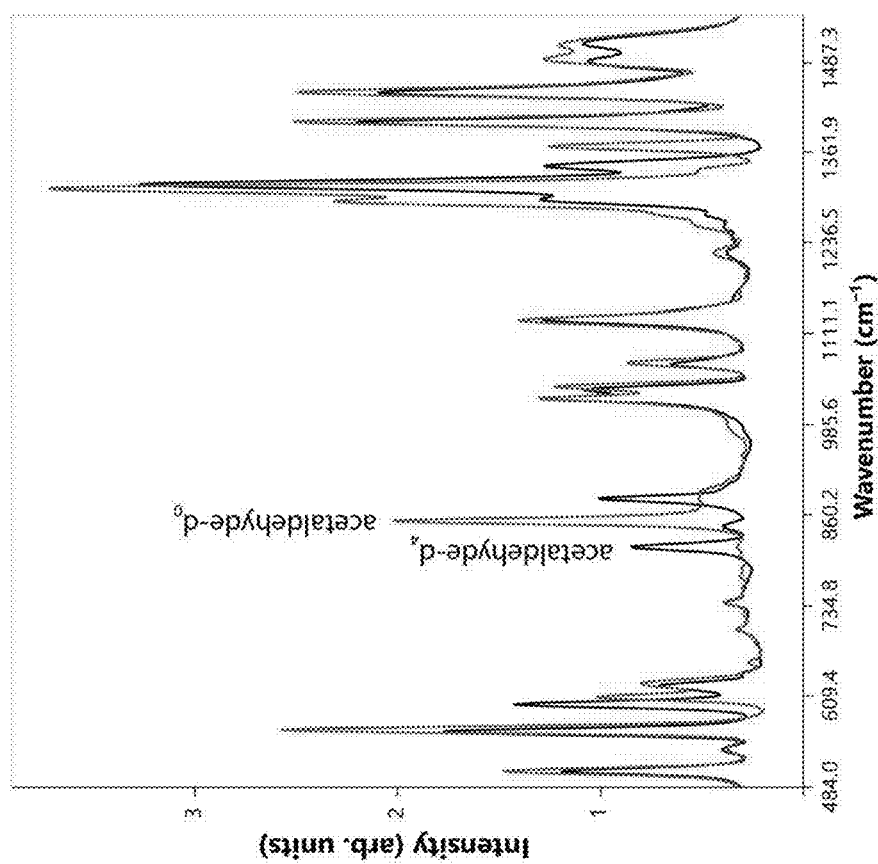
FIG. 10 shows portions of Raman spectra for a deuterated aldehyde-MBTH compounds.
Figure 11:
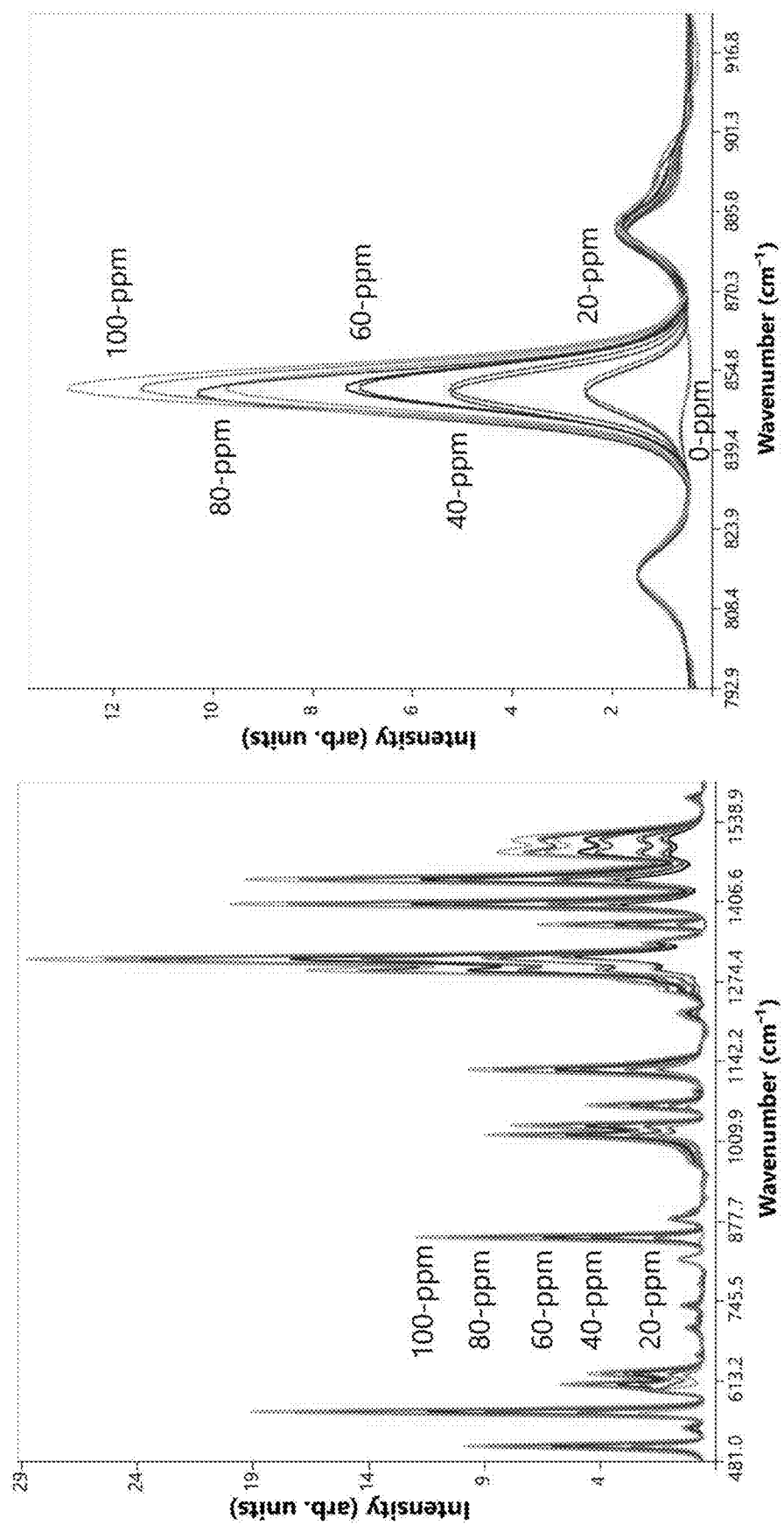
FIGS. 11 and 12 shows portions of Raman spectra for aldehyde-MBTH compounds at different concentrations.
Figure 12:
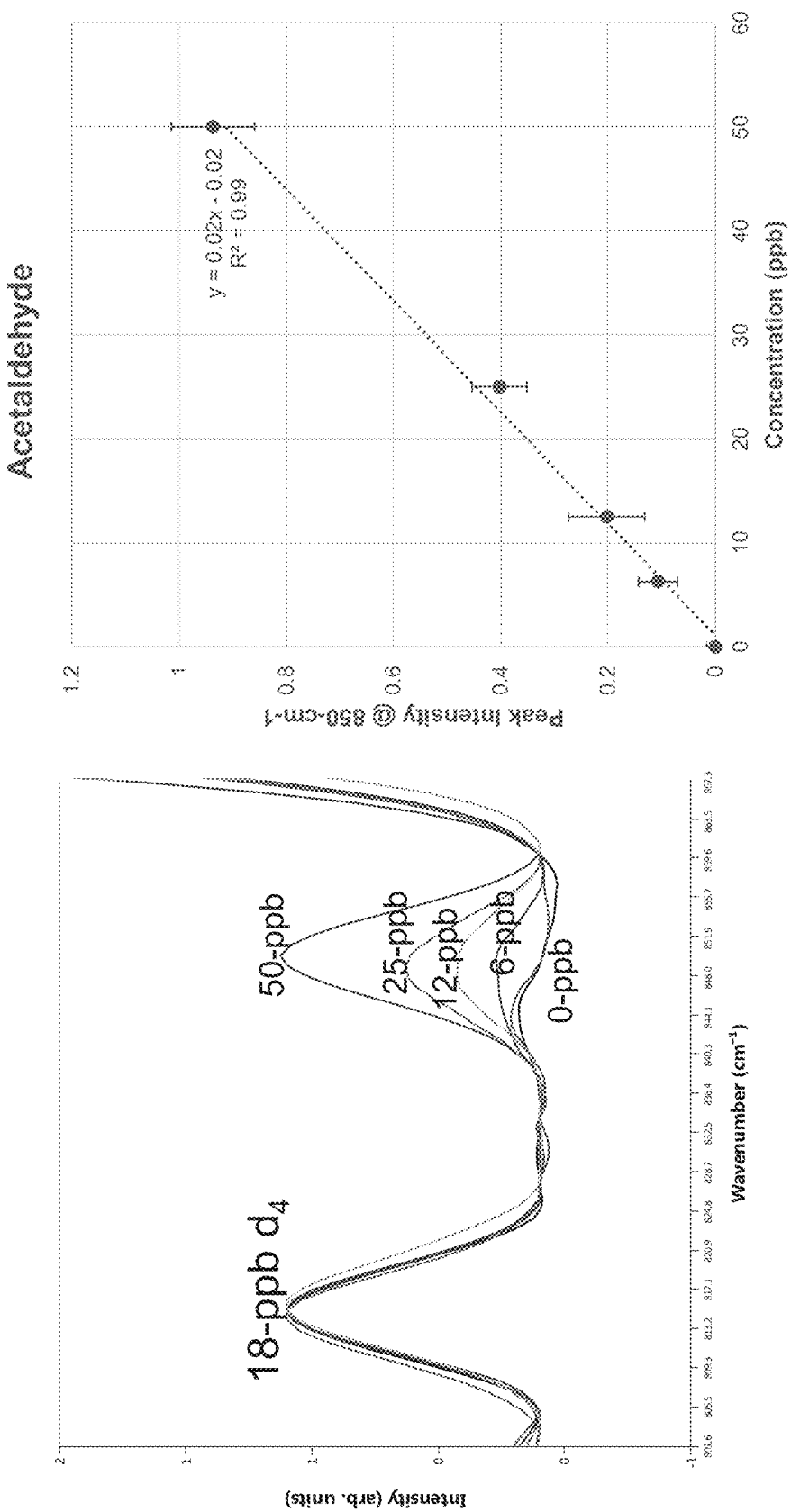
Figure 13:
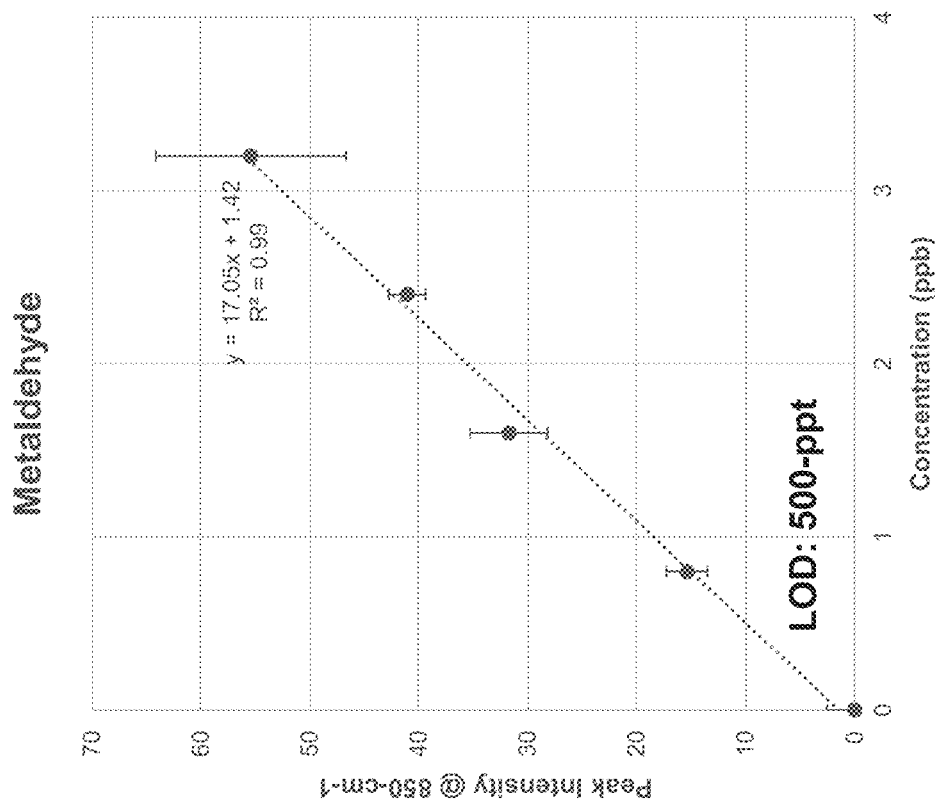
FIG. 13 shows portions of Raman spectra for reaction products of MBTH (a colorimetric dye) and acetaldehyde (a compound reactive with the colorimetric dye), wherein the acetaldehyde is obtained from metaldehyde at different concentrations converted to acetaldehyde.
Figure 13:
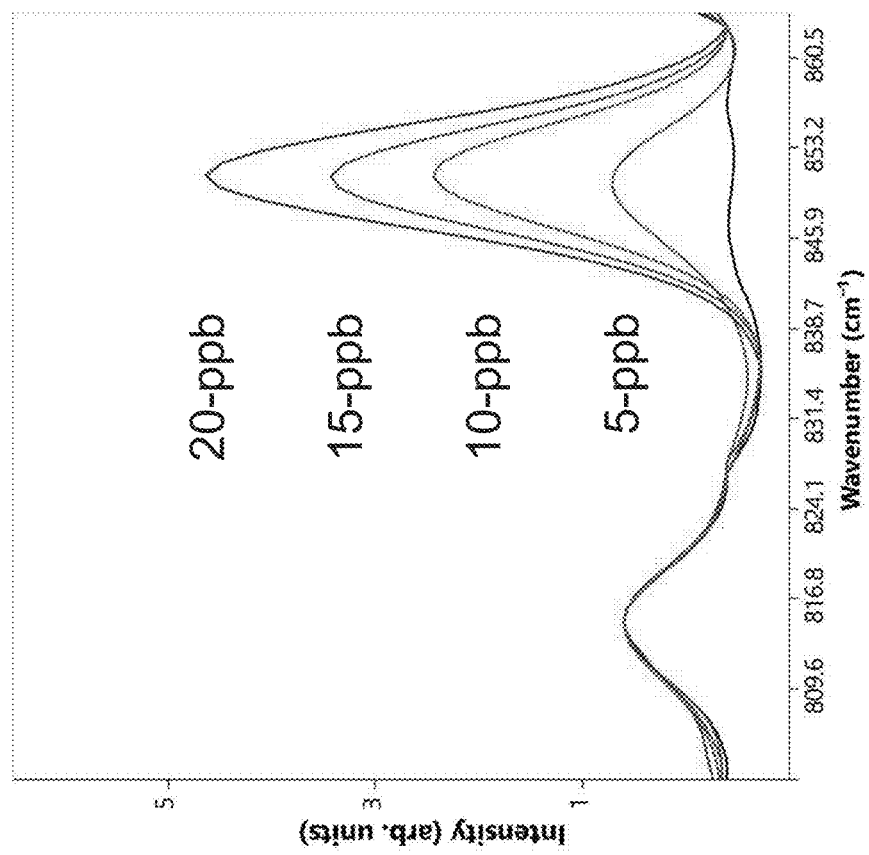

An isotopologue internal standard is used as a reference. The isotopologue may be, for example, a deuterated aldehyde. The isotopolgue has a different Raman spectra (see FIG. 10) and, when added to the sample in a known amount, provides a reference that enhances the accuracy of concentration measurements, for example by ratiometric scaling based on the known amount of the isotopolgue added to the sample and scaling of the intensity of peaks to concentrations. For example, size of the peak relative to concentration for acetaldehyde is shown in FIGS. 11 and 12 and for metaldehyde (after conversion to aldehyde) in FIG. 13. Preferably, glass vials or trays etc. are used to hold the samples because some plastics (i.e. PET) release aldehydes.

To measure aldehydes that do not react with MBTH, for example metaldehyde, the analyte can be converted to a form that does react with MBTH. In an exemplary process to measure metaldehyde: add know amount of isotopolgue such as metaldehyde-$d_{16}$ to the sample; add MBTH to sample; add MBTH to sample, wait 60 minutes at 90° C.; add $Fe^{3+}$ to sample; wait 30 minutes; mix with gold nanoparticles; measure Raman spectrum.

A similar approach can be used to measure other contaminants that are conventionally measured with colorimetric dyes. Most colorimetric dyes have an amine group. Other examples of analytes measure with colorimetric dyes, wherein the analyte-colorimetric dye compound can be measured by is Raman spectra, preferably also with an isotpologue internal reference standard, include: selenium, ammonia, chlorinated solvents, lead and alcohols.

Our approach to metaldehyde analysis proceeds by digesting to acetaldehyde and then using an acetaldehyde measurement procedure. The digestion procedure starts by mixing the colorimetric indicator dye with the sample along with an internal standard. The sample is heated to approximately 70° C. for 60 minutes. This procedure breaks the metaldehyde into its constituent aldehyde, which then react with the MTBH dye. The preferred internal standard for metaldehyde analysis is metaldehyde-$d_{16}$; however, given the measurement is of acetaldehyde, then acetaldehyde-$d_4$ is also acceptable.

Real-world water samples contain acetaldehyde naturally; our measurements show approximately 2-ppb in river water samples. To determine the metaldehyde concentration in this type of water sample, we add acetaldehyde-$d_4$ as an internal standard followed by the dye, then split the sample into two portions. One portion is heated to digest the aldehyde; the second portion is not heated, so that only the naturally occurring aldehyde reacts. The difference between the two measurements determines the metaldehyde concentration.

Figure 14:
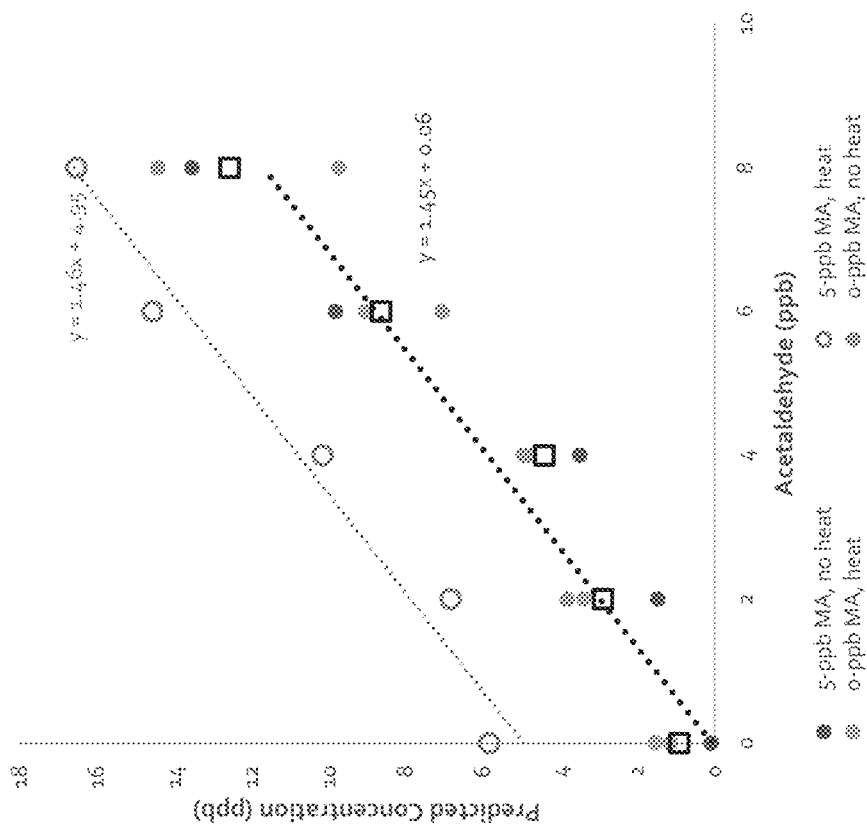
FIG. 14 shows measurements of aldehyde concentrations in water samples containing various background concentrations of aldehyde and 5-ppb metaldehyde, with and without heating the metaldehyde to convert it to aldehyde.

Examples of measurements are shown in FIG. 14. Samples were produced with background concentrations of acetaldehyde at 0-8 ppb. Some samples had 5 ppb metaldehyde added. Some samples were heated. Measurements clustered around the lower line were samples without heat and 0 or 5 ppb metaldehyde and samples with heat but no metaldehyde. Samples clustered around the upper line were samples with heat and 5 ppb metaldehyde. These results indicate that heating a sample with metaldehyde produced an increase in measured concentration of acetaldehyde approximately equal to the amount of metaldehyde added. This indicates that metaldehyde can be measured by converting it to acetaldehyde and also that a background level of acetaldehyde in the sample can be measured in an unheated sample and subtracted from a measurement of a heated sample to determine the amount of metaldehyde in a sample containing a metaldehyde-acetaldehyde mixture.

An alternative approach to eliminate the acetaldehyde interference when quantifying an analyte such as metaldehyde is to introduce a compound such as bisulfite that forms an adduct with aldehydes. The approach binds the native aldehyde (such as native acetaldehyde, corresponding to a first amount of a compound reactive with a colorimetric dye) so that only the analyte, for example metaldehyde (after conversion to acetaldehyde, corresponding to a second amount of the compound reactive with a colorimetric dye), reacts with the colorimetric dye such as MBTH. The metaldehyde is quantified by performing a ratiometric analysis of peaks or bands within a Raman spectrum corresponding to a reaction product of the colorimetric dye (such as MBTH) and the second amount of the compound reactive with the colorimetric dye (such as acetaldehyde converted from metaldehyde) and an isotopologue (for example a deuterated aldehyde, which may be part of a reaction product of the isotopologue and the colorimetric dye).

Spectral analysis to determine the metaldehyde concentration starts with smoothing and baseline subtraction. The spectrum is then scaled to the internal standard peak at 815-$cm^{-1}$. If the internal standard peak is not present, the users is presented with an error message. The spectral data is passed through a multivariate analysis method, such as a Multivariate Adaptive Regressive Splines algorithm, to determine the final concentration.

Spectral analysis for acetaldehyde is complicated by a peak in the MTBH spectrum that partially overlaps the acetaldehyde signal. This extra peak may be eliminated through spectral subtraction techniques. An spectrum from a sample containing zero acetaldehyde can be subtracted from the raw data to provide a proper baseline signal. This processed data can then be analyzed for analyte concentration.

Figure 8:
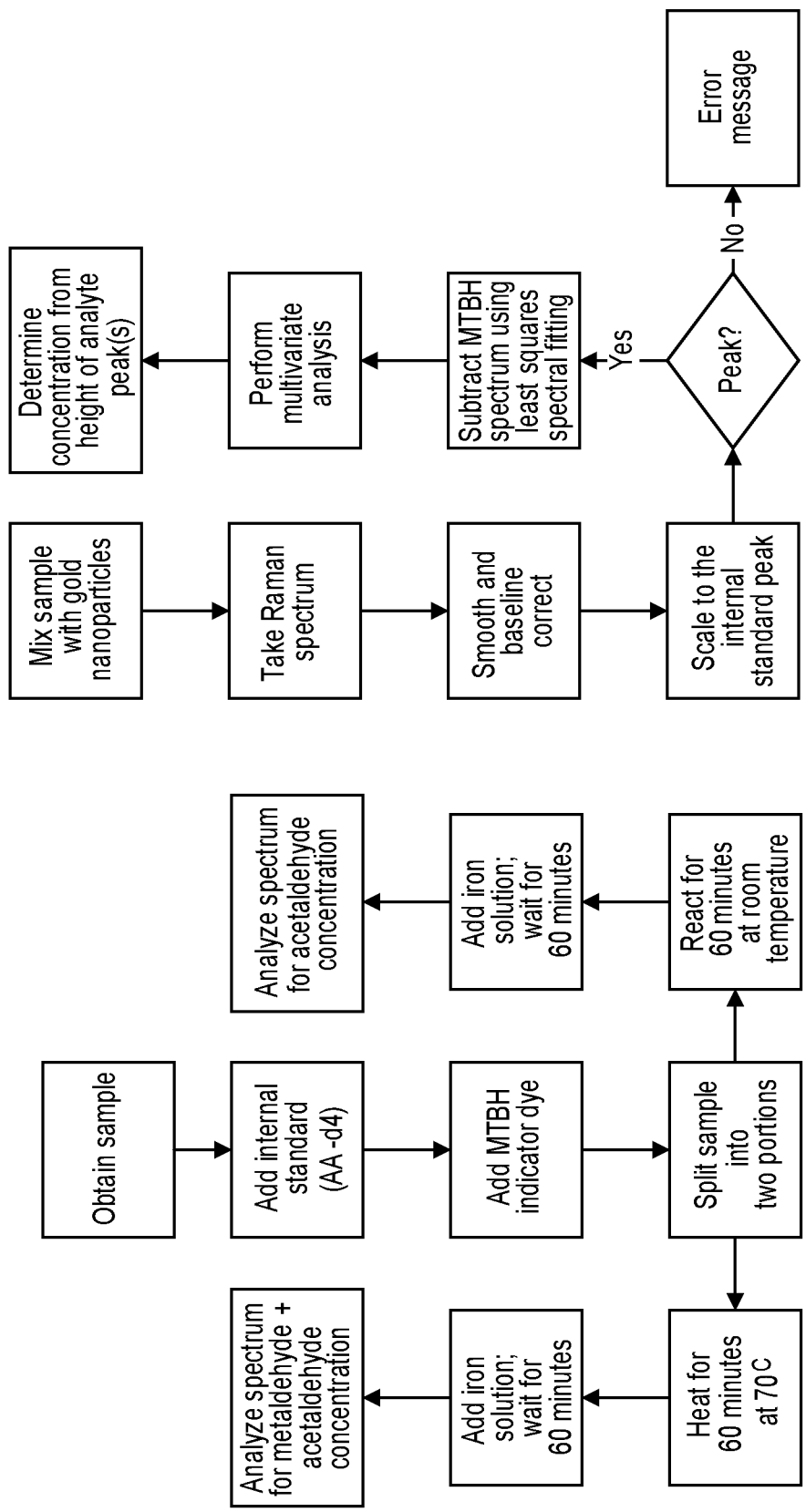
FIG. 8 shows an aldehyde analysis process.

FIG. 8 shows an aldehyde analysis process as discussed above.

U.S. application Ser. No. 14/198,163 filed on Mar. 5, 2014 is incorporated herein by reference.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, many additional amines may be detected using a similar approach. These amines include methylamine, diethanolamine, methyldiethanolamine, dimethylethanolamine, diisopropylamine, cyclohexylamine, morpholine, and methoxypropylamine. Other anions including nitrate, chromate, thiosulfate, phosphate, and carbonate may be detected using similar approaches to the method presented for perchlorate analysis.

All such variations are considered to be within the scope and spirit of the present invention as defined by the following claims and their legal equivalents.

I claim:

1. A method of measuring an amount of an analyte in water, the water containing the analyte and a first amount of a compound reactive with a colorimetric dye, the method comprising the steps of:
    obtaining a first sample of the water of a known volume;
    mixing a known amount of an isotopologue with the first sample;
    mixing the colorimetric dye with the first sample;
    treating the analyte to form a second amount of the compound reactive with the colorimetric dye after binding the first amount of the compound reactive with the colorimetric dye to form an adduct to eliminate interference caused by the first amount of the compound reactive with the colorimetric dye;
    mixing Raman-scattering nanoparticles with the first sample to produce a mixture;
    producing a Raman spectrum of the mixture; and,
    performing a ratiometric analysis of peaks or bands within the Raman spectrum corresponding to a reaction product of the colorimetric dye and the second amount of the compound reactive with the colorimetric dye and the isotopologue to quantify the analyte,
    wherein the analyte is an aldehyde.

2. The method of claim 1 comprising preparing a second sample of the water with the colorimetric dye and not with the compound reactive with the colorimetric dye, and subtracting a spectrum of the second sample from a spectrum of the first sample.

3. The method of claim 1 wherein the colorimetric dye is N-methylbenzothiazolinon-2-hydrazone (MBTH), the analyte is metaldehyde, the compound reactive with the colorimetric dye is acetaldehyde, and the step of treating the analyte comprises heating of the first sample to convert metaldehyde to acetaldehyde.

4. The method of claim 2 comprising subtracting a spectrum for MBTH.

5. The method of claim 2 comprising reacting the first amount of the compound reactive with the colorimetric dye in the second sample to form an adduct.

6. The method of claim 1 wherein the compound reactive with the colorimetric dye is acetaldehyde and the first amount of acetaldehyde is reacted with a bisulfite.

7. The method of claim 1 wherein the isotopologue is an isotopologue of the analyte or of the compound reactive with the colorimetric dye.

* * * * *